US011254630B2

(12) United States Patent
Alshahrani et al.

(10) Patent No.: US 11,254,630 B2
(45) Date of Patent: Feb. 22, 2022

(54) METHOD OF SEPARATING LINEAR ALPHA OLEFINS

(71) Applicant: SABIC GLOBAL TECHNOLOGIES B.V., Bergen op Zoom (NL)

(72) Inventors: Dafer Mubarak Alshahrani, Riyadh (SA); Shahid Azam, Riyadh (SA); Abdullah Saad Al-Dughaither, Riyadh (SA); Abdulmajeed Mohammed Al-Hamdan, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/470,753

(22) PCT Filed: Dec. 19, 2017

(86) PCT No.: PCT/IB2017/058155
§ 371 (c)(1),
(2) Date: Jun. 18, 2019

(87) PCT Pub. No.: WO2018/116174
PCT Pub. Date: Jun. 28, 2018

(65) Prior Publication Data
US 2019/0345079 A1   Nov. 14, 2019

Related U.S. Application Data

(60) Provisional application No. 62/436,181, filed on Dec. 19, 2016.

(51) Int. Cl.
*C07C 7/04*     (2006.01)
*B01D 3/14*    (2006.01)
(Continued)

(52) U.S. Cl.
CPC .............. *C07C 7/04* (2013.01); *B01D 3/143* (2013.01); *C07C 11/04* (2013.01); *C07C 11/08* (2013.01); *C07C 11/107* (2013.01)

(58) Field of Classification Search
None
See application file for complete search history.

(56) References Cited

U.S. PATENT DOCUMENTS 3,751,518 A * 8/1973 Hagan .................. C07C 2/88
585/313
5,817,902 A * 10/1998 Xie ..................... B01J 10/002
585/328

(Continued)

FOREIGN PATENT DOCUMENTS

CN    1609083 A    4/2005
CN    106132533    11/2016
(Continued)

OTHER PUBLICATIONS

International Search Report for International Application No. PCT/IB2017/058155, International Filing Date Dec. 19, 2017. dated Mar. 28, 2018, 5 pages.
(Continued)

Primary Examiner — Philip Y Louie
(74) Attorney, Agent, or Firm — Norton Rose Fulbright US LLP

(57) ABSTRACT

A method of separating linear alpha olefins, comprising: passing a feed stream comprising linear alpha olefins through a first column; distributing a C4− fraction to a top portion of the first column; withdrawing a C6+ fraction from a bottom portion of the first column and passing the C6+ fraction through a second column; distributing a C12+ fraction to a bottom portion of the second column; withdrawing a C10− fraction from a top portion of the second column and passing the C10− fraction through a third (Continued)

column, wherein the C10− fraction is substantially free of polymer; and distributing a C6 fraction to a top portion of the third column.

17 Claims, 1 Drawing Sheet

(51) Int. Cl.
*C07C 11/04* (2006.01)
*C07C 11/08* (2006.01)
*C07C 11/107* (2006.01)

(56) References Cited

U.S. PATENT DOCUMENTS

| | | |
|---|---|---|
| 7,476,775 B2 | 1/2009 | Kreischer |
| 8,492,492 B2 | 7/2013 | Mills et al. |
| 2007/0185360 A1 | 8/2007 | Buchanan et al. |
| 2007/0185362 A1 | 8/2007 | Lattner et al. |
| 2010/0030000 A1 | 2/2010 | Emoto et al. |
| 2014/0012059 A1 | 1/2014 | Vinel et al. |
| 2015/0299069 A1* | 10/2015 | Azam ............... C07C 2/34 585/513 |
| 2017/0175014 A1 | 6/2017 | Prevost et al. |

FOREIGN PATENT DOCUMENTS

| | | |
|---|---|---|
| WO | 2013158223 A1 | 10/2013 |
| WO | WO 2017/115255 | 7/2017 |
| WO | WO 2017/115308 | 7/2017 |
| WO | WO 2018/116174 | 6/2018 |

OTHER PUBLICATIONS

Written Opinion for International Application No. PCT/IB2017/058155, International Filing Date Dec. 19, 2017. dated Mar. 28, 2018, 5 pages.
Office Action issued in corresponding Iranian Patent Application No. 139850140003002145, dated Aug. 26, 2020.
Office Action issued in counterpart Indian Patent Application No. 201917017315, dated Aug. 13, 2020.
Office Action issued in Corresponding Chinese Application No. 201780071867.8, dated Jun. 18, 2021 (No English translation).

* cited by examiner

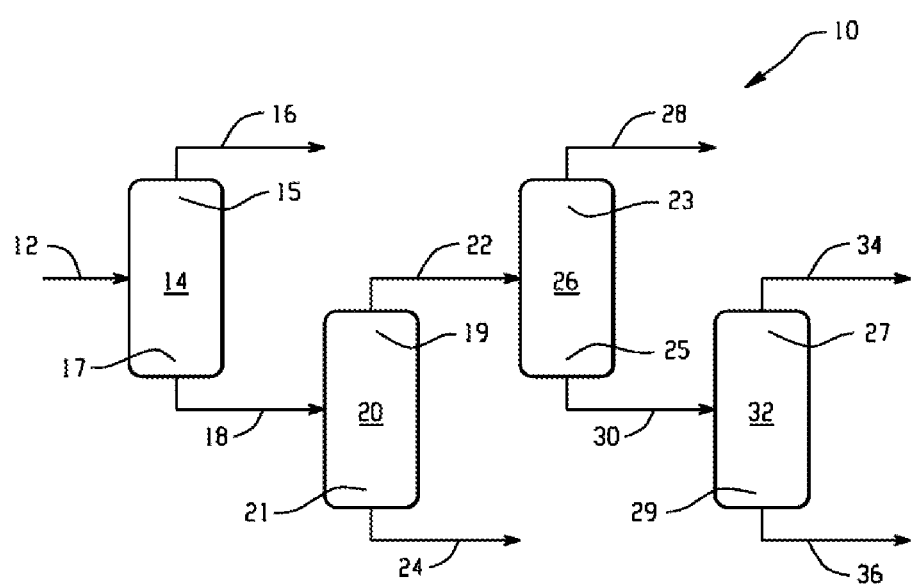

METHOD OF SEPARATING LINEAR ALPHA OLEFINS

CROSS REFERENCE TO RELATED APPLICATIONS

This application is a National Stage application of PCT/IB2017/058155, filed Dec. 19, 2017, which claims the benefit of U.S. Application No. 62/436,181, filed Dec. 19, 2016, both of which are incorporated by reference in their entirety herein.

BACKGROUND

Distillation is one of the most common liquid-liquid separation processes. Distillation works via the application and removal of heat to exploit differences in relative volatility. The heat causes components with lower boiling points and higher volatility to be vaporized, leaving less volatile components as liquids. Mixtures with high relative volatilities are often easier to separate, while mixtures with low relative volatilities can be difficult to separate effectively.

In particular, the distillation of oligomerization products presents many challenges. For example, oligomerization products often comprise a mixture of both hydrocarbons and dissolved polymers. Accordingly, any distillation equipment used to separate oligomerization products must be customized in a manner that allows for the presence of dissolved polymer. For example, such distillation columns must comprise special materials that can withstand high temperatures. Furthermore, the bottom portion of the columns must be extended in length in order to increase the velocity of polymeric streams and prevent polymer settling. Whenever oligomerization products are distilled for the purposes of isolating particular fractions, all the distillation columns involved in the separation must be customized in this manner Such modifications are costly and negatively affect the overall efficiency of the process.

Thus, there is a need for a method of isolating pure product fractions from a mixture of hydrocarbons and dissolved polymer that requires only a minimal number of distillation columns be modified to handle polymers.

SUMMARY

Disclosed, in various embodiments, are methods of separating linear alpha olefins.

A method of separating linear alpha olefins, comprises: passing a feed stream comprising linear alpha olefins through a first column; distributing a C4− fraction to a top portion of the first column; withdrawing a C6+ fraction from a bottom portion of the first column and passing the C6+ fraction through a second column; distributing a C12+ fraction to a bottom portion of the second column; withdrawing a C10− fraction from a top portion of the second column and passing the C10− fraction through a third column, wherein the C10− fraction is substantially free of polymer; and distributing a C6 fraction to a top portion of the third column.

A system for separating linear alpha olefins, comprises: a first column; a second column; and a third column; wherein the first column is configured to: receive a feed stream comprising linear alpha olefins; distribute a C4− fraction to a top portion of the first column; release a C6+ fraction from a bottom portion of the first column; and pass the C6+ fraction to the second column; wherein the second column is configured to: receive the C6+ fraction; distribute a C12+ fraction to a bottom portion of the second column; release a C10− fraction from a top portion of the second column; and pass the C10− fraction to the third column, wherein the C10− fraction is substantially free of polymer; wherein the third column is configured to: receive the C10− fraction; and distribute a C6 fraction to a top portion of the third column.

These and other features and characteristics are more particularly described below.

BRIEF DESCRIPTION OF THE DRAWINGS

The following is a brief description of the drawings wherein like elements are numbered alike and which are presented for the purposes of illustrating the exemplary embodiments disclosed herein and not for the purposes of limiting the same.

The Figure is a schematic diagram representing a method for separating linear alpha olefins.

DETAILED DESCRIPTION

The method disclosed herein can isolate pure product fractions from a mixture of hydrocarbons and dissolved polymer so that only a minimal number of distillation columns are modified to handle polymers. For example, the present method can isolate linear alpha olefin fractions at greater than or equal to 99% purity by weight. For example, the present method can isolate hexene and toluene fractions at greater than or equal to 99% purity by weight. In the present method, the distillation columns do not all have to be capable of handling polymers. For example, not all the distillation columns have a bottom portion extended in length in order to increase the velocity of polymeric streams and prevent polymer settling. Furthermore the distillation columns used in the method disclosed herein can comprise a material other than a special heat resistant material. Each of these features contributes to a lower cost associated with separating linear alpha olefins when the feed stream comprises dissolved polymer.

A method of separating linear alpha olefins can include passing a feed stream comprising linear alpha olefins through a first column. A C4− fraction can be distributed to a top portion of the first column and can then be withdrawn from the first column. A C6+ fraction can be distributed to a bottom portion of the first column and can then be withdrawn from the first column. The C6+ fraction can be passed through a second column. A C12+ fraction can be distributed to a bottom portion of the second column and can then be withdrawn from the second column. A C10− fraction can be distributed to a top portion of the second column and can then be withdrawn from the second column. The C10− fraction can be substantially free of polymer. For example, the C10− fraction can comprise less than or equal to 1 parts per million polymer. The C10− fraction can be passed through a third column. A C6 fraction can be distributed to a top portion of the third column and can then withdrawn from the third column. The C6 fraction can be greater than or equal to 99% pure by weight. The third column can be capable of handling polymers without modification.

The method disclosed herein can include a feed stream. The source of the feed stream can be the product of an ethylene oligomerization process. For example, the source of the feed stream can be an oligomerization reactor liquid outlet stream. The feed stream can comprise a mixture of hydrocarbons. The feed stream can comprise a mixture of hydrocarbons with dissolved polymer. For example, the feed stream can comprise linear alpha olefins. For example, the feed stream can comprise methane, ethylene, ethane, 1-butene, 1-hexene, aromatics, alkanes, olefins, 1-octene, 1-decene, 1-dodecene, or a combination comprising at least one of the foregoing. The feed stream can also comprise by-products and/or impurities. For example, the feed stream can comprise catalyst deactivator agents and catalyst decomposition materials. The feed stream can comprise a mixture of hydrocarbons and dissolved polymer. For example, the feed stream can comprise polyethylene.

The feed stream can be passed through a first column. For example, the first column can be a separation column, for example a distillation column. The first column can distribute a C4– fraction to a top portion of the first column. For example, the C4– fraction can comprise methane, ethylene, ethane, 1-butene, or a combination comprising at least one of the foregoing. The C4– fraction can be withdrawn from the first column through a C4– stream.

The first column can distribute a C6+ fraction to a bottom portion of the first column. For example, the C6+ fraction can comprise hexene. The C6+ fraction can be withdrawn from the bottom portion of the first column through a C6+ stream. A pressure within the first column can be 0 kiloPascal to 4000 kiloPascals, for example, 250 kiloPascals to 3500 kiloPascals, for example, 300 kiloPascals to 3000 kiloPascals. A temperature of the C4– stream can be –100° C. to 50° C., for example, –75° C. to 25° C., for example, –70° C. to 20° C. A temperature of the C6+ stream can be greater than a melting point of a polymer dissolved in the C6+ stream. For example, a temperature of the C6+ stream can be 100° C. to 350° C., for example, 125° C. to 325° C., for example, 130° C. to 300° C.

The C6+ stream can be passed through a second column, which can be a separation column, for example a distillation column. The second column can distribute a C10– fraction to a top portion of the second column. For example, the C10– fraction can comprise 1-octene and/or 1-decene. The C10– fraction can be substantially free of polymer. For example, the C10– fraction can comprise less than or equal to 1 parts per million polymer. The C10– fraction can be withdrawn from the second column through a C10– stream.

The second column can distribute a C12+ fraction to a bottom portion of the second column. For example, the C12+ fraction can comprise 1-dodecene. The C12+ fraction can also comprise by-products and/or impurities. For example, the C12+ fraction can comprise catalyst deactivator agents and catalyst decomposition. The C12+ fraction can comprise a mixture of hydrocarbons and dissolved polymer. For example, the C12+ fraction can comprise polyethylene. The C12+ fraction can be withdrawn from the bottom portion of the second column through a C12+ stream. A pressure within the second column can be 0 kiloPascal to 2500 kiloPascals, for example, 0 kiloPascal to 2000 kiloPascals, for example, 0 kiloPascal to 1500 kiloPascals. A temperature of the C10– stream can be 50° C. to 300° C., for example, 60° C. to 275° C., for example, 70° C. to 250° C. A temperature of the C12+ stream can be 50° C. to 450° C., for example, 75° C. to 425° C., for example, 100° C. to 400° C.

The C10– stream can be passed through a third column. For example, the third column can be a separation column, for example a distillation column. The third column can distribute a C6 fraction to a top portion of the third column. For example, the C6 fraction can comprise greater than or equal to 99% hexene by weight. The C6 fraction can be substantially free of solvent, by-products, and deactivated catalyst. For example, the C6 fraction can comprise less than or equal to 1 parts per million of these impurities. The C6 fraction can be withdrawn from the third column through a C6 stream.

The third column can distribute a C7+ fraction to a bottom portion of the third column. For example, the C7+ fraction can comprise a solvent, e.g., aromatics, alkanes, olefins, or a combination comprising at least one of the foregoing. For example, the solvent can be toluene. The C7+ fraction can be withdrawn from the bottom portion of the third column through a C7+ stream. A pressure within the third column can be 0 kiloPascal to 2500 kiloPascals, for example, 0 kiloPascal to 2000 kiloPascals, for example, 0 kiloPascal to 1500 kiloPascals. A temperature of the C6 stream can be 50° C. to 300° C., for example, 60° C. to 275° C., for example, 70° C. to 250° C. A temperature of the C7+ stream can be 50° C. to 450° C., for example, 75° C. to 425° C., for example, 100° C. to 400° C. The third column can be capable of processing the material without modifications. Stated another way, the third column does not need to be suitable for handling polymers. For example, the third column can be free of high temperature resistance material such as polysulfone, polyimide, polyether, or a combination comprising at least one of the foregoing, for example, polyphenylene sulfone, polyethylene sulfone, polyether ether ketone, polyether ketone, polyether imide, or a combination comprising at least one of the foregoing. The third column can be free from a bottom portion that is extended in length in order to increase the velocity of polymeric streams and prevent polymer settling.

The C7+ stream can be passed through a fourth column. For example, the fourth column can be a distillation column. The fourth column can distribute a C7 fraction to a top portion of the fourth column. For example, the C7 fraction can comprise greater than or equal to 99% toluene by weight. The C7 fraction can be substantially free of solvent, by-products, and deactivated catalyst. For example, the C7 fraction can comprise less than or equal to 1 parts per million of these impurities. The C7 fraction can be withdrawn from the fourth column through a C7 stream.

The fourth column can distribute a C8-C10 fraction to a bottom portion of the fourth column. The C8-C10 fraction can be withdrawn from the bottom portion of the fourth column through a C8-C10 stream. A pressure within the fourth column can be 0 kiloPascal to 2500 kiloPascals, for example, 0 kiloPascal to 2000 kiloPascals, for example, 0 kiloPascal to 1500 kiloPascals. A temperature of the C7 stream can be 50° C. to 300° C., for example, 60° C. to 275° C., for example, 70° C. to 250° C. A temperature of the C8-C10 stream can be 50° C. to 450° C., for example, 75° C. to 425° C., for example, 100° C. to 400° C. The fourth column can be capable of processing the material without modifications. Stated another way, the fourth column does not need to be suitable for handling polymers. For example, the fourth column can be free of high temperature resistance material, such as polysulfone, polyimide, polyether, or a combination comprising at least one of the foregoing, for example, polyphenylene sulfone, polyethylene sulfone, polyether ether ketone, polyether ketone, polyether imide, or a combination comprising at least one of the foregoing. The fourth column can be free from a bottom portion that is extended in length in order to increase the velocity of polymeric streams and prevent polymer settling.

In the method, columns downstream from the second column can be free of high temperature resistant materials. For example, columns downstream from the second column can be free from a material selected from polysulfone, polyimide, polyether, or a combination comprising at least one of the foregoing. For example, the material can be selected from polyphenylene sulfone, polyethylene sulfone, polyether ether ketone, polyether ketone, polyether imide, or a combination comprising at least one of the foregoing.

In the method, columns downstream from the second column can be free from a bottom portion that is extended lengthwise as compared to the first column or the second column. For example, columns downstream the second column can be 10% smaller lengthwise as compared to the first column or the second column.

In the method, columns downstream from the second column can be free of a high temperature coating and/or a special design of column internals.

A more complete understanding of the components, processes, and apparatuses disclosed herein can be obtained by reference to the accompanying drawings. These figures (also referred to herein as "FIG.") are merely schematic representations based on convenience and the ease of demonstrating the present disclosure, and are, therefore, not intended to indicate relative size and dimensions of the devices or components thereof and/or to define or limit the scope of the exemplary embodiments. Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

Referring now to the Figure, this simplified schematic diagram represents a reactor scheme 10 in a method for separating linear alpha olefins. The method can include passing a feed stream 12 through a first column 14. For example, the feed stream 12 can comprise a mixture of hydrocarbons and dissolved polymer. For example, the feed stream 12 can comprise hexene and/or polyethylene. The first column 14 can be a separation column, for example a distillation column. The first column 14 can distribute a C4− fraction to a top portion 15 of the first column 14. For example, the C4− fraction can comprise methane, ethylene, ethane, 1-butene, or a combination comprising at least one of the foregoing. The C4− fraction can be withdrawn from the first column 14 through C4− stream 16. The first column 14 can distribute a C6+ fraction to a bottom portion 17 of the first column 14. For example, the C6+ fraction can comprise hexene. The C6+ fraction can be withdrawn from the bottom portion 17 of the first column 14 through C6+ stream 18.

The C6+ stream can be passed through a second column 20. For example, the second column 20 can be a distillation column. The second column 20 can distribute a C10− fraction to a top portion 19 of the second column 20. For example, the C10− fraction can comprise 1-octene and/or 1-decene. The C10− fraction can be substantially free of polymer. For example, the C10− fraction can comprise less than or equal to 1 parts per million polymer. The C10− fraction can be withdrawn from the second column 20 through C10− stream 22. The second column 20 can distribute a C12+ fraction to a bottom portion 21 of the second column 22. For example, the C12+ fraction can comprise 1-dodecene and dissolved polymer. The C12+ fraction can be withdrawn from the bottom portion 21 of the second column 20 through C12+ stream 24.

The C10− stream 22 can be passed through a third column 26. For example, the third column 26 can be a distillation column. The third column 26 can distribute a C6 fraction to a top portion 23 of the third column 26. The C6 fraction can comprise greater than or equal to 99% hexene by weight. The C6 fraction can be substantially free of solvent, by-products, and deactivated catalyst. For example, the C6 fraction can comprise less than or equal to 1 parts per million of these impurities. The C6 fraction can be withdrawn from the third column 26 through the C6 stream 28. The third column 26 can distribute a C7+ fraction to a bottom portion 25 of the third column 26. For example, the C7+ fraction can comprise solvent. The C7+ fraction can be withdrawn from the bottom portion 25 of the third column 26 through C7+ stream 30. The third column 26 does not need to comprise a material that will allow it handle polymers. Stated another way, the third column 26 can comprise a material other than that which will allow it to handle polymers. For example, the third column 26 can be free of high temperature resistant material and can be free from a bottom portion that is extended in length.

The C7+ stream 30 can be passed through a fourth column 32. For example, the fourth column 32 can be a distillation column. The fourth column 32 can distribute a C7 fraction to a top portion 27 of the fourth column 32. For example, the C7 fraction can comprise greater than or equal to 99% toluene by weight. The C7 fraction can be substantially free of solvent, by-products, and deactivated catalyst. For example, the C7 fraction can comprise less than or equal to 1 parts per million of these impurities. The C7 fraction can be withdrawn from the fourth column 32 through the C7 stream 34. The fourth column 32 can distribute a C8-C10 fraction to a bottom portion 29 of the column 32. The C8-C10 fraction can be withdrawn from the bottom portion 29 of the fourth column 32 through C8-C10 stream 36. The fourth column 32 does not need to comprise a material that will allow it handle polymers. Stated another way, the fourth column 32 can comprise a material other than that which will allow it to handle polymers. For example, the fourth column 32 can be free of high temperature resistant material and can be free from a bottom portion that is extended in length.

The following example is merely illustrative of the method of separating linear alpha olefins disclosed herein and is not intended to limit the scope hereof. Unless otherwise stated, the example was based upon simulations.

Example

Example 1

In this example, simulation software was used to measure the contents of the various streams as shown in FIG. 1. The stream numbers correspond to the streams shown in the Figure. Temperature (T) was measured in degrees Celsius, pressure was measured in bar gauge (barg), and mass flow was measured in kilograms per hour (kg/hr).

TABLE 1

Simulation Data

| | Stream No. | | | | |
|---|---|---|---|---|---|
| | 12 | 16 | 18 | 22 | 24 |
| T (° C.) | 36.4 | −19.2 | 217.1 | 116.4 | 260.4 |
| P (barg) | 14.19 | 31.99 | 14.39 | 1.34 | 1.59 |
| Mass Flow (kg/hr) | 50999.8 | 15970.8 | 34808.9 | 34580.5 | 228.4 |
| Mass Fraction | | | | | |
| Ethyelene | 0.154597 | 0.453573 | 0 | 0 | 0 |
| Butene-1 | 0.179533 | 0.537487 | 0.000200 | 0.000196 | 0 |
| Hexene-1 | 0.245558 | 0.000750 | 0.370040 | 0.361784 | 0 |
| Octene-1 | 0.001137 | 0 | 0.001715 | 0.003816 | 0 |
| Decene-1 | 0.011455 | 0 | 0.017279 | 0.043532 | 0.003447 |
| Dodecene-1 | 0.003208 | 0 | 0.004839 | 0.000029 | 0.712032 |
| Solvent | 0.400273 | 0 | 0.603801 | 0.590443 | 0 |
| Spent Catalyst | 0.001409 | 0 | 0.002126 | 0 | 0.284521 |

| | Stream No. | | | |
|---|---|---|---|---|
| | 28 | 30 | 34 | 36 |
| T (° C.) | 67.7 | 123.5 | 115.0 | 198.7 |
| P (barg) | 0.14 | 0.39 | 0.14 | 1.29 |
| Mass Flow (kg/hr) | 12510.8 | 22069.7 | 20433.5 | 1636.2 |
| Mass Fraction | | | | |
| Ethyelene | 0 | 0 | 0 | 0 |
| Butene-1 | 0.000540 | 0 | 0 | 0 |
| Hexene-1 | 0.999458 | 0.000337 | 0.000324 | 0 |
| Octene-1 | 0 | 0.005034 | 0.000484 | 0.074617 |
| Decene-1 | 0 | 0.045939 | 0 | 0.920019 |
| Dodecene-1 | 0 | 0.000025 | 0 | 0.000611 |
| Solvent | 0.000001 | 0.948404 | 0.999192 | 0.000500 |
| Spent Catalyst | 0 | 0 | 0 | 0 |

As can be seen in Table 1, the C10− stream (stream no. 22 according to the Figure) is free from polymer (e.g., ethylene), the C6 fraction (stream no. 28 according to the Figure) is substantially free of solvent, spent catalyst, and by-products.

The methods disclosed herein include(s) at least the following aspects:

The methods disclosed herein include(s) at least the following aspects:

Aspect 1: A method of separating linear alpha olefins, comprising: passing a feed stream comprising linear alpha olefins through a first column; distributing a C4− fraction to a top portion of the first column; withdrawing a C6+ fraction from a bottom portion of the first column and passing the C6+ fraction through a second column; distributing a C12+ fraction to a bottom portion of the second column; withdrawing a C10− fraction from a top portion of the second column and passing the C10− fraction through a third column, wherein the C10− fraction is substantially free of polymer; and distributing a C6 fraction to a top portion of the third column.

Aspect 2: The method of Aspect 1, wherein a source of the feed stream is a product of an ethylene oligomerization process or wherein the feed stream is a product of a mixture of hydrocarbons with dissolved polymer.

Aspect 3: The method of any of the preceding aspects, wherein the feed stream comprises aromatics, alkanes, olefins, or a combination comprising at least one of the foregoing, preferably, wherein the feed stream comprises methane, ethylene, ethane, 1-butene, 1-hexene, aromatics, 1-octene, 1-decene, 1-dodecene, catalyst deactivator agent, catalyst de-composition, polymer, or a combination comprising at least one of the foregoing.

Aspect 4: The method of any of the preceding aspects, wherein the feed stream comprises 1-hexene and/or polyethylene.

Aspect 5: The method of any of the preceding aspects, further comprising withdrawing the C4− fraction from the top portion of the first column.

Aspect 6: The method of any of the preceding aspects, further comprising withdrawing the C12+ fraction from the bottom portion of the second column.

Aspect 7: The method of any of the preceding aspects, further comprising withdrawing a C7+ fraction from a bottom portion of the third column.

Aspect 8: The method of Aspect 7, further comprising passing the C7+ fraction through a fourth column.

Aspect 9: The method of Aspect 8, further comprising withdrawing a C7 fraction from a top portion of the fourth column.

Aspect 10: The method of Aspect 8, further comprising withdrawing a C8-C10 fraction from a bottom portion of the fourth column.

Aspect 11: The method of any of the preceding aspects, wherein the C4– fraction comprises methane, ethylene, ethane, 1-butene, or a combination comprising at least one of the foregoing.

Aspect 12: The method of any of the preceding aspects, wherein the C12+ fraction comprises 1-dodecene, catalyst deactivator agent, catalyst de-composition, polymer, or a combination comprising at least one of the foregoing.

Aspect 13: The method of any of the preceding aspects, wherein the C10– fraction comprises 1-octane, 1-decene, less than 1 part per million polymers, or a combination comprising at least one of the foregoing.

Aspect 14: The method of any of the preceding aspects, wherein the C6 fraction comprises greater than or equal to 99% hexene by weight.

Aspect 15: The method of any of the preceding aspects, wherein the C6 fraction comprises less than one part per million of solvent, by-products, and deactivated catalyst.

Aspect 16: The method of any of the preceding aspects, wherein columns downstream from the second column are free of high temperature resistant materials, preferably wherein columns downstream from the second column are free from a material selected from polysulfone, polyimide, polyether, or a combination comprising at least one of the foregoing, preferably wherein the material is selected from polyphenylene sulfone, polyethylene sulfone, polyether ether ketone, polyether ketone, polyether imide, or a combination comprising at least one of the foregoing.

Aspect 17: The method of any of the preceding aspects, wherein columns downstream from the second column are free from a bottom portion that is extended lengthwise as compared to the first column or the second column, preferably wherein columns downstream the second column are 10% smaller lengthwise as compared to the first column or the second column.

Aspect 18: The method of any of the preceding aspects, wherein columns downstream from the second column are free of a high temperature coating and/or a special design of column internals.

Aspect 19: The method of any of the preceding aspects, wherein a pressure within the first column is 250 kiloPascals to 3500 kiloPascals.

Aspect 20: A system for separating linear alpha olefins, comprising: a first column; a second column; and a third column; wherein the first column is configured to: receive a feed stream comprising linear alpha olefins; distribute a C4– fraction to a top portion of the first column; release a C6+ fraction from a bottom portion of the first column; and pass the C6+ fraction to the second column; wherein the second column is configured to: receive the C6+ fraction; distribute a C12+ fraction to a bottom portion of the second column; release a C10– fraction from a top portion of the second column; and pass the C10– fraction to the third column, wherein the C10– fraction is substantially free of polymer; wherein the third column is configured to: receive the C10– fraction; and distribute a C6 fraction to a top portion of the third column.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). The notation "±10%" means that the indicated measurement can be from an amount that is minus 10% to an amount that is plus 10% of the stated value. The terms "front", "back", "bottom", and/or "top" are used herein, unless otherwise noted, merely for convenience of description, and are not limited to any one position or spatial orientation. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like.

All cited patents, patent applications, and other references are incorporated herein by reference in their entirety. However, if a term in the present application contradicts or conflicts with a term in the incorporated reference, the term from the present application takes precedence over the conflicting term from the incorporated reference While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A method of separating linear alpha olefins, comprising:
   passing a feed stream comprising ethylene, linear alpha olefins comprising at least C4, C6, C10, and C12 linear alpha olefins, and spent catalyst through a first column;
   distributing a C4– fraction to a top portion of the first column;

withdrawing a C6+ fraction comprising C6+ linear alpha olefins and the spent catalyst, from a bottom portion of the first column and passing the C6+ fraction through a second column;

distributing a C12+ fraction comprising C12 linear alpha olefins and the spent catalyst to a bottom portion of the second column;

withdrawing a C10− fraction comprising C6-C10 linear alpha olefins from a top portion of the second column and passing the C10− fraction through a third column, wherein the C10− fraction comprises less than or equal to 1 parts per million of polymer; and distributing a C6 fraction to a top portion of the third column, wherein the C6 fraction comprises greater than or equal to 99% hexene by weight.

2. The method of claim 1, wherein the feed stream comprises a mixture of hydrocarbons with dissolved polymer.

3. The method of claim 1, wherein the feed stream comprises aromatics, alkanes, olefins other than linear alpha olefins, or a combination comprising at least one of the foregoing.

4. The method of claim 1, wherein the feed stream comprises polyethylene.

5. The method of claim 1, further comprising withdrawing the C4− fraction from the top portion of the first column.

6. The method of claim 1, wherein the feed stream further comprises aromatics.

7. The method of claim 1, further comprising withdrawing a C7+ fraction from a bottom portion of the third column.

8. The method of claim 7, further comprising passing the C7+ fraction through a fourth column.

9. The method of claim 1, wherein the feed stream further comprises methane, ethane, 1-butene, catalyst deactivator agent, catalyst decomposition, or a combination comprising at least one of the foregoing.

10. The method of claim 1, wherein the C4− fraction comprises methane.

11. The method of claim 1, wherein the C12+ fraction further comprises catalyst deactivator agent.

12. The method of claim 1, wherein the C10− fraction comprises 1-octene.

13. The method of claim 1, wherein the C6 fraction comprises less than one part per million of solvent, by-products, and spent catalyst.

14. The method of claim 1, wherein columns downstream from the second column are free of high temperature resistant materials.

15. The method of claim 1, wherein columns downstream from the second column are free from a bottom portion that is extended lengthwise as compared to the first column or the second column.

16. The method of claim 1, wherein a pressure within the first column is 250 kiloPascals to 3500 kiloPascals.

17. The method of claim 1, wherein columns downstream from the second column are free from a material selected from the group consisting of a polysulfone, a polyimide and a polyether, or a combination thereof.

* * * * *